United States Patent [19]

Degenkolb et al.

[11] 4,312,732
[45] Jan. 26, 1982

[54] METHOD FOR THE OPTICAL MONITORING OF PLASMA DISCHARGE PROCESSING OPERATIONS

[75] Inventors: Eugene O. Degenkolb, Basking Ridge; James E. Griffiths; Cyril J. Mogab, both of New Providence, all of N.J.

[73] Assignee: Bell Telephone Laboratories, Incorporated, Murray Hill, N.J.

[21] Appl. No.: 128,837

[22] Filed: Mar. 10, 1980

Related U.S. Application Data

[63] Continuation of Ser. No. 719,259, Aug. 31, 1976, abandoned.

[51] Int. Cl.$^3$ .......................... C23C 15/00; C23F 1/00
[52] U.S. Cl. ................................. 204/192 E; 156/643
[58] Field of Search .................. 204/164, 192 E, 298; 156/345, 643; 356/437, 72

[56] References Cited

U.S. PATENT DOCUMENTS 3,664,942  5/1972  Havas et al. ........................ 204/192

OTHER PUBLICATIONS

J. E. Greene et al., "Glow-Discharge Optical Spectroscopy for the Analysis of Thin Films", *J. Appl. Phys.*, vol. 44, pp. 2509-2513 (1973).
J. E. Greene et al., "Glow Discharge Optical Spectroscopy for Monitoring Sputter Deposited Film Thickness", *J. Vac. Sci. Technol.*, vol. 10, pp. 1144-1149 (1973).

*Primary Examiner*—Aaron Weisstuch
*Attorney, Agent, or Firm*—Bruce S. Schneider; Allen N. Friedman

[57] ABSTRACT

The endpoints of plasma discharge processing operations (e.g., plasma stripping of photoresists and plasma etching) are determined by monitoring the light produced in the space surrounding the object being processed. The optical monitor includes a wavelength selective device which is adjusted to transmit light from a selected excited species, which includes particles from the surface being processed. The surface includes a layer of one material overlaying a second material. If the selected excited species includes particles of the first material, then the endpoint of the removal operation occurs when the monitored intensity falls below a predetermined threshold level. When the selected excited species includes particles of the second material, then the endpoint occurs when the monitored intensity rises above a preselected threshold level.

5 Claims, 3 Drawing Figures

METHOD FOR THE OPTICAL MONITORING OF PLASMA DISCHARGE PROCESSING OPERATIONS

This application is a continuation of application Ser. No. 719,259, filed Aug. 31, 1976, now abandoned.

BACKGROUND OF THE INVENTION

1. Field of the Invention

The invention is in the field of manufacturing processes related to material removal. It particularly relates to optical control methods and apparatus concerned with such manufacturing processes in solid state device fabrication.

2. Brief Description of the Prior Art

There are, in commercial use, a number of etching, stripping, or other material removal operations which employ plasma discharges and charged particles produced by such discharges. Such processes are becoming more and more widely used in the fabrication of solid state devices, to displace wet chemical processing. In these processes the surface to be treated is exposed to a plasma discharge or to a beam of accelerated particles from the plasma. Most of these processes fall into two main groups. In the first of these groups the removal of material from the body being treated is produced by a chemical reaction between active species in the plasma and the material of the body, with the formation of volatile reaction products. The volatile products are then pumped away. The other principal group involves the removal of material from the body being treated, by momentum transfer from accelerated particles in the plasma. In either case it is commercially observed that light in the infrared, visible and ultraviolet regions of the spectrum is produced in the space surrounding the body. It has been noted in the past that both the intensity and color of the emitted light, in many of these processes, changes during the processing operation. However, several different chemical and physical phenomena are occurring simultaneously in the discharge region, so that it may be difficult to draw exact conclusions from the observation of the emitted light.

SUMMARY OF THE INVENTION

A sensitive optical monitoring technique has been developed to determine the endpoint of plasma discharge related material removal processes. The subject processes involve the removal of a layer of one material overlaying a second material in the substrate body. In many cases it is important to halt the processes as soon as possible after the upper layer is completely removed, in order to minimize the possibly damaging effects of the exposure of the underlying material to the plasma particles.

In this optical monitoring technique, light from the space surrounding the body is passed through a frequency selective device and directed onto an optical detector. The frequency and bandwidth of the frequency selective device are selected to correspond to the radiation from a particular excited species, which includes material from the body being processed. One exemplary commercial process is the removal of photoresist layers from the surface of solid state device materials by exposure of the layer to an oxygen plasma. The photoresist layer consists principally of hydrocarbons, which are oxidized by the oxygen in the plasma. During this oxidation, carbon monoxide in an electronic excited state is one of the reaction products. Intense radiation from several of the excited states of this species is observed in the ultraviolet and in the visible. If the frequency selective device is set to pass light in one of these molecular bands, the completion of the stripping operation is determined, as the intensity of that radiation falls below a predetermined threshold level. The frequency selective device permits the desired reaction to be observed independently of the many other reactions which are simultaneously taking place in the reaction chamber. A light frequency can also be selected which corresponds to a species including material from below the layer being removed. For example, in the removal of portions of a metallic layer from the surface of a body of tin doped gallium arsenide, the frequency selective device can be set to correspond to one of the excitations of tin in the appropriate region of the spectrum. In such a case the removal of the metal layer is signified by the increase of the detected optical signal above a predetermined threshold level. When the endpoint of the process has been reached the process can be immediately halted.

DETAILED DESCRIPTION OF THE INVENTION

Plasma Discharge Processing

Figure 1:
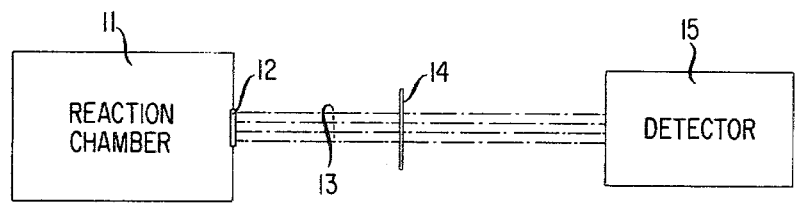
FIG. 1 is a schematic view of an exemplary device of the invention including a transmission filter.

Plasma discharge processing involves the removal of material from the surface of the body through the interaction of the surface with particles produced in a plasma discharge. In one form of such processing a chemical reaction takes place between the material of the surface and the particles of the plasma, producing volatile species which are pumped away. One area in which this process is used is in the dry stripping of photoresist films from the surface of solid state device substrates through exposure of the film to an oxygen plasma. An exemplary apparatus, in which this may be done, is disclosed in the U.S. Pat. No. 3,875,068 issued Apr. 1, 1975.

Another major type of plasma discharge processing involves removal of the material from the surface by direct momentum transfer from accelerated particles from the plasma to particles of the surface material. In one such process, often termed plasma sputtering, the substrate is exposed to an rf plasma of a relatively inert gas and surface material is removed by the bombardment of the surface by accelerated particles in the plasma. In another process, commercially referred to as ion milling, charged particles are extracted from a plasma and further accelerated to form an ion beam which is directed at the body being processed.

Optical Monitoring

In all of the above-mentioned plasma discharge processing procedures, light is produced in the space surrounding the surface being processed. This light can be produced as a result of several different phenomena. Light may be produced by simple recombination of the primary gaseous species in which the plasma is generated. Particles from the substrate may be ejected in an excited state which decays to produce light. Particles from the surface may, also, be produced in chemical combination with material from the plasma. Such compounds may be produced in an excited state or they may subsequently be excited by collisions in the plasma. Such excited states result in the production of light during decay to a state of lower energy. It is characteristic of such excited species that excited states of single atoms produce radiation with a half width of the order of an Angstrom or less, whereas excited states of molecules produce broader bands which may extend over of the order of 100 Angstroms. The emission spectra of a great many species of interest have been investigated and may be found in general texts such as "The Identification of Molecular Spectra" by R. W. B. Pearse and A. G. Gaydon, Chapman & Hall, Ltd., 3rd Edition, 1965 and "Atomic Energy Levels," 1, Nat. Bur. Stds. (1949) by C. E. Moore and "MIT Wavelength Tables" by G. R. Harrison, MIT Press, 1969. The center frequency of the frequency selective device employed in the herein disclosed process can be selected from such texts depending upon the chemical nature of the body being processed and the plasma being employed in the processing. Alternately, the emission bands present can be determined by spectral analysis of the emitted light. The bandwidth of the frequency selective device is similarly selected in accordance with the known emission spectra of the subject species. It is usually advantageous to select as large a portion of a particular excitation band as possible in order to achieve increased signal strength. However narrowing of the selected band may be indicated by the desire to avoid neighboring emissions produced by other species in the plasma resulting from other reactions which may simultaneously be taking place.

In order to admit as much of the desired radiation as possible while eliminating unwanted radiation, the half width of the frequency selective device used should be no greater than 150 Angstroms. In order to achieve increased selectivity, particularly where the desired band is known to be near emission lines corresponding to other species, it is preferred that the half width be no greater than 25 Angstroms. For still greater selectivity, particularly when the subject species is atomic as opposed to molecular, the half width may be 5 Angstroms or less. Limitation of the band width also serves to reduce the unwanted contribution of continuous background radiation. The selected radiation can be in the infrared, the visible or the ultraviolet region of the spectrum. However the visible and ultraviolet are preferred over the infrared region because of the relatively greater intensity of thermal radiation in the infrared region, which tends to mask the emission lines.

Apparatus

FIG. 1 shows, in schematic form, an exemplary apparatus of the invention. The body to be treated is located within a reaction chamber 11, which includes some means for generating a plasma discharge such that particles which produce the removal of material come in contact with the bodies being treated. The bodies are supported within the reaction chamber 11 by some convenient support means, such that the desired portion of the body is exposed to the active particles. The reaction chamber also includes a window 12 for extracting a portion of the electromagnetic radiation, which is produced within the reaction chamber by the plasma and by the interaction between the plasma and the body being treated. The extracted light 13 passes through a frequency selective device, such as filter 14, and is incident on a detector 15. Many suitable types of filters are known in the art. These include dielectric interference filters, which may be obtained with very narrow transmission half widths and dye filters, which are generally much broader in transmission.

Figure 2:
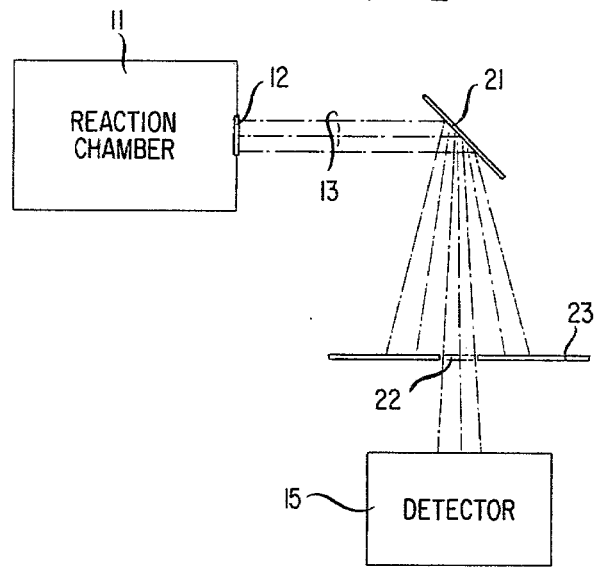
FIG. 2 is a schematic view of an exemplary device of the invention including a dispersive reflector and frequency selective slit.
Figure 3:
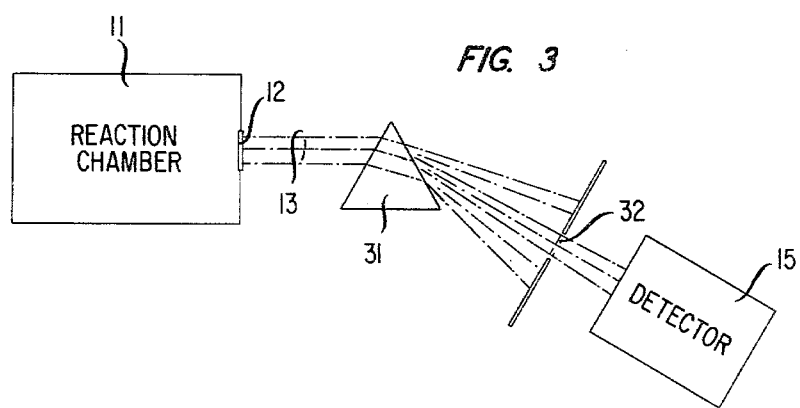
FIG. 3 is a schematic view of an exemplary device of the invention including a frequency dispersive transmitter and frequency selective slit.

In FIG. 2 the frequency selective device includes a dispersive reflector 21 and a frequency limiting aperture 22 such as a slit in an opaque screen 23. Dispersive reflectors include both ruled and halographic gratings. FIG. 3 illustrates the use of a dispersive transmitter such as a prism 31 together with a frequency limiting aperture 32. The apparatus of FIGS. 2 and 3 offer the advantage of the ability to easily change the center frequency of the detected radiation by changing the relative position of the slit 22, 32 and dispersive element 21, 31. The apparatus of FIG. 1, on the other hand is capable of much more compact construction. In such an apparatus frequency changes may be accomplished by the substitution of different filters 14.

The detector 15 used may be any one of a number of known broad band detectors of optical radiation. These include photomultiplier tubes and solid state radiation detectors such as diodes, photovoltaic cells and non-rectifying photo conductive materials such as cadmium sulfide.

For the control of photoresist stripping operations, usefully intense emission bands due to carbon monoxide are located at 2977 Angstroms, 4835 Angstroms and 5198 Angstroms and a usefully intense emission band due to the hydroxyl group is located at 2830 Angstroms. Using a monochromator with a concave holographic grating set to transmit the carbon monoxide line at 5198 Angstroms, it was possible to sensitively observe the final clean up of photoresist residues.

What is claimed is:

1. A method for fabricating a device comprising the steps of
    (a) subjecting a body to a plasma discharge wherein said body comprises a resist material in intimate contact with an underlying material in a substrate body;
    (b) passing a portion of the electromagnetic radiation produced by said plasma discharge into a radiation detector which produces an output signal dependent upon the intensity of said portion of radiation; and
    (c) removing said body from contact with the plasma discharge after said output signal passes a predetermined threshold value characterized in that the portion of electromagnetic radiation is a frequency limited portion of half width no greater than 150 Angstroms including radiation of a frequency corresponding to radiation from a preselected excited species including particles resulting from chemical combination of entities from said body with entities from said plasma discharge.

2. The process of claim 1 wherein said resist material comprises a photoresist layer.

3. The process of either claim 1 or 2 wherein said particles resulting from chemical combinations emanate from the reaction of entities from said plasma discharge with said resist material.

4. The process of claim 1 wherein said body comprises a metal.

5. The process of claim 1 wherein said body comprises a semiconductor material.

* * * * *